Figure 1:
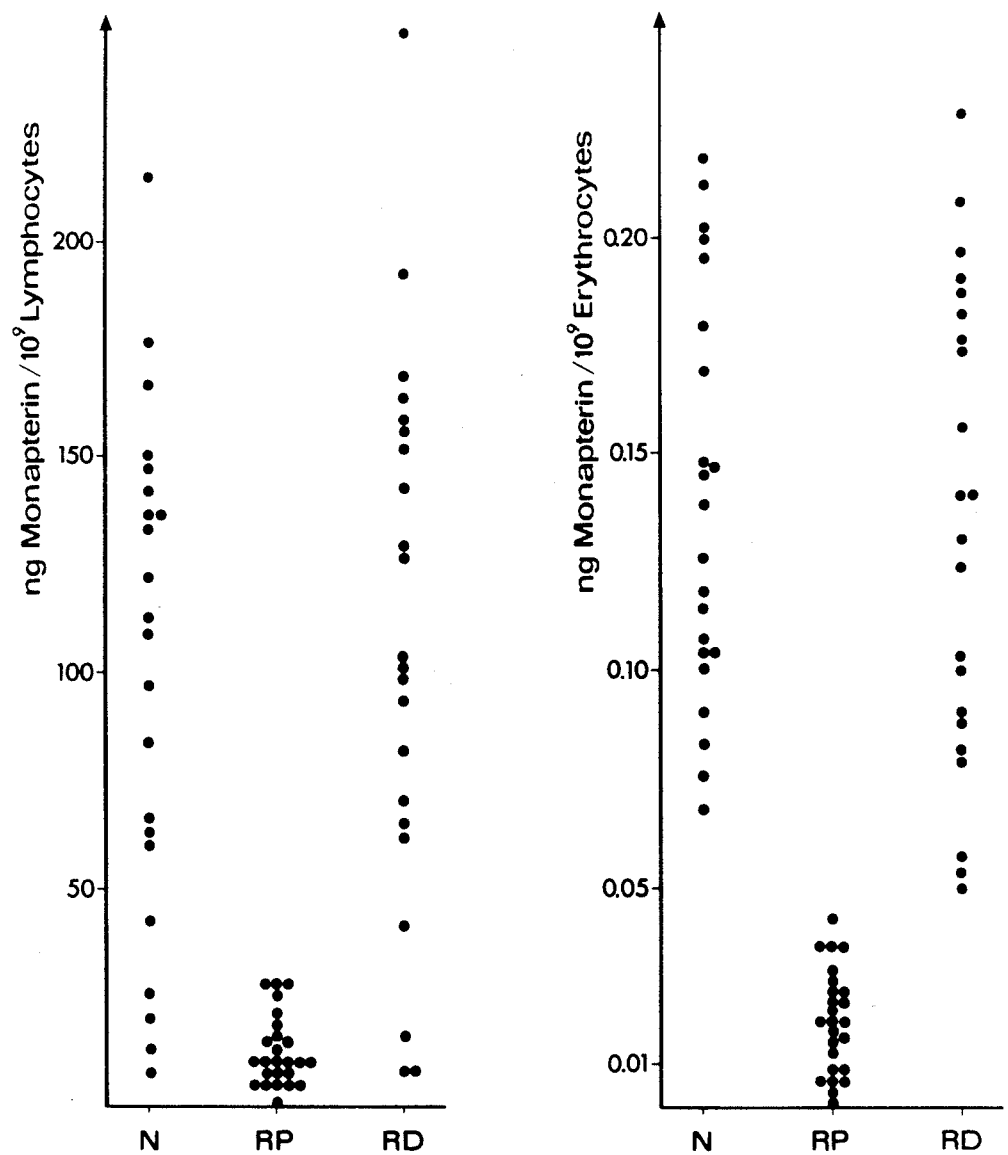

United States Patent [19]

Cremer

[11] Patent Number: 4,943,575

[45] Date of Patent: Jul. 24, 1990

[54] PHARMACEUTICAL COMPOSITION FOR THE TREATMENT OF GENETICALLY CAUSED DEGENERATIVE RETINA DISEASES AND A PROCESS FOR THE PREPARATION THEREOF

[75] Inventor: Gertrud Cremer, Münster, Fed. Rep. of Germany

[73] Assignee: Pharm-Allergan GmbH, Karlsruhe, Fed. Rep. of Germany

[21] Appl. No.: 155,400

[22] Filed: Feb. 12, 1988

[30] Foreign Application Priority Data

Feb. 13, 1987 [EP] European Pat. Off. ........ 87102094.7

[51] Int. Cl.$^5$ .............................................. A61K 31/50
[52] U.S. Cl. ...................................... 514/249; 514/912
[58] Field of Search ................. 514/249, 258, 262, 912

[56] References Cited

U.S. PATENT DOCUMENTS

| | | | |
|---|---|---|---|
| 4,425,344 | 1/1984 | Horlington | 514/249 |
| 4,425,345 | 1/1984 | Horlington et al. | 514/249 |
| 4,425,346 | 1/1984 | Horlington et al. | 514/249 |
| 4,746,668 | 5/1988 | Sato et al. | 514/912 |

FOREIGN PATENT DOCUMENTS

| | | | |
|---|---|---|---|
| 59524 | 9/1982 | European Pat. Off. | 514/249 |
| 2082455 | 3/1982 | United Kingdom | 514/249 |

OTHER PUBLICATIONS

Ann. Optamol. Clin. Ocul., 97:143–153 (1971).

*Primary Examiner*—Douglas W. Robinson
*Assistant Examiner*—Zohreh A. Fay
*Attorney, Agent, or Firm*—Sughrue, Mion, Zinn, Macpeak & Seas

[57] ABSTRACT

The present invention relates to the use of pteridines and/or biochemical precursors thereof or xanthinoxidase inhibitors for the treatment of genetically caused degenerative retina diseases, in particular retinopathia pigmentosa (RP), and a pharmaceutical composition containing the same.

7 Claims, 1 Drawing Sheet

PHARMACEUTICAL COMPOSITION FOR THE TREATMENT OF GENETICALLY CAUSED DEGENERATIVE RETINA DISEASES AND A PROCESS FOR THE PREPARATION THEREOF

The invention concerns the use of pteridines and/or biochemical precursors thereof or xanthinoxidase inhibitors for the treatment of genetically caused degenerative retina diseases, especially retinopathia pigmentosa (hereinafter "RP").

In the following specification the invention is described for the treatment of RP, because RP is the most frequent degenerative retina disease. It is estimated that throughout the world 3 million people suffer from one of the various forms of RP.

In the case of RP, this is a disease of the retina which, in the advanced state, may lead to loss of the field of view and finally to total blindness. It is a degenerative process which is usually inherited. In the course of the illness, there is a contraction of the vessels, an optic atrophy and a deterioration of the nervous elements of the retina together with a deposit of pigment (osseous cell-type pigmentation) which progresses from the periphery to the center of the eye.

The progression of RP from the first occurrence of symptoms to strong orientation difficulties lasts on the average approximately 8 years and frequently begins in puberty. In contrast to the normal vision which has a panorama view of approximately 180° to 200°, the RP patient does not see objects outside the direction of view or sees them only in sections. The RP patient experiences very consciously the fact that his field of view is constantly reduced. He is also very aware of the hopelessness of his state, because neither a therapy for prophylaxis nor for the treatment or even the healing of RP are known. As a rule, the RP patients are so greatly adversely affected at between 40 and 50 years of age that they are practically blind. Tests which have been made to stop the progress of RP by the administration of 11-cis-vitamin A have had no demonstrable success. In accordance with the present state of knowledge one must assume that the prognosis of RP is unfavorable.

Under the above-discussed circumstances, it is obvious that there is a strong requirement for a pharmaceutical composition for the treatment of genetically caused degenerative retina diseases of the type of RP.

The present invention is based on the finding that in the case of retinopathia pigmentosa patients, certain pteridines are significantly reduced compared to normal healthy persons. Therefore, the present invention is based on the new recognition that in the case of retinopathia pigmentosa patients, the lack of pteridines, which appears to be of significance for the pathogenisis of this disease, can be compensated for by the administration of pteridines and/or by influencing the enzymes which destroy pteridines.

Therefore, the invention concerns the use of pteridines and/or biochemical precursors thereof or of an xanthinoxidase inhibitor for the treatment of genetically caused degnerative retina diseases.

Allopurinol is an uricostatic agent, which as a xanthinoxidase inhibiting substance, counteracts the increased formation of urea (hyperuricaemia) in the case of gout patients. Allopurinol has the formula 1H-pyrazolo(3,4-d)pyrimidine-4-ol

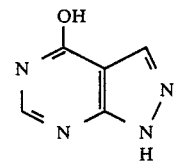

This is a pharmaceutical which has been proven and used over the years.

In pteridines, there is a pyrazine ring which is condensed with a pyrimidine ring. Pteridines are found in nature and are isolated from the wings of butterflies and also from eyes of insects.

Because of the asymmetrical carbon atoms contained in them, pteridines are stereoisomers. The invention also includes the respective diastereoisomers and racemates. It is known in the case of pharmacological active ingredients that frequently only one predetermined diastereoisomer form is effective, or that one diastereomer form has the greater efficiency compared with the other diastereomer form. All these forms are included in the present invention.

The following, for example, are pteridines which are suitable for the present invention: monapterine, sepiapterine, xanthopterine. In accordance with the present state of knowledge monapterine is preferred. However it should be assumed that because of the biochemical conversion of one pteridine into another pteridine, the pteridine structure and the free availability of pteridine in the body ar important.

Triampterene is a mild diuretic having a pteridine structure. Therefore, triampterene can also be considered for the treatment of RP. Similarly to allopurinol, triampterene is a pharmaceutical which has already been introduced into medical practice, although with a totally different indication than in the case of the present invention, so that the side-effects of this pharmaceutical are already known and can be taken into consideration during the therapy.

The acidic addition salts of pteridine are also included in the present invention. The pteridines are as a rule very hard to dissolve in water. The solubility is improved by the salt formation. Although it must be assumed that the salt-free form has the desired pharmaceutical effect, the pteridines can be present in the salt form, for example as a hydrochloride salt, in the pharmaceuticals, because these salts are converted in the body into the free form. The difficulty of solubility in water can be utilized for the preparation of slow-release compositions. This is of significance, in particular, in the case of topical application directly into the eye.

Purines are precursors for pteridines. Therefore, the application of such precursors for the treatment of RP is taken into consideration within the framework of the present invention and is included in this invention. The dosage employed in the present invention can be varied within a wide range. The low solubility of the majority of pteridines in water and therefore, in the tissue of the human body as well, allows a wide range of dosage with a systemic modus operandi. The dosage is adjusted depending on the weight and on the remaining state of the patient. Administration once per day or several times per day of the oral forms of the present invention are possible.

To the specialist, it is evident that further adjuvants and active ingredients which are known in ophthalmology can be worked into the respective pharmaceutical preparations. An example of one of the numerous possibilities benzalconiumchloride.

The formulation of the pharmaceutical composition is carried out in the manner which is usual for the respective application form and is familiar to pharmacists and to galenicists. For topical applications, firstly the classical forms of eye drops and eye salves are taken into consideration. The eye drops consists, for example, of a solution or suspension of the active ingredient in water for injection purposes, with polyvinyl alcohol as the carrier substance, and with sodium chloride, sodium disulfite, potassium hydrogen, sodium monohydrogen phosphate, sodium hydroxide as well as benzalconium chloride and edetic acid, disodium salt $2H_2O$ as preservatives.

An eye salve contains preferably white vasiline, liquid paraffin, amerchol CAB, water for injection purposes and chlorobutanol for preservation.

Because RP patients are subject to the longterm administration of the active ingredients of the present invention, the above mentioned slow-release form is of particular interest, because by using it the frequency of application can be reduced in a manner which is pleasing to the patient. For a topical slow-release form ocular inserts in which the active ingredients are found as a solution, suspension or as solids are taken into consideration.

Drops and salves must be applied several times each day for application on the eye, because the pharmaceuticals or the pharmaceutical form itself which is released is relatively quickly removed from the place of application by the movement of the eyelids and by the lacrimal fluid. The embeddings in the form of ocular inserts which are inserted in the conjunctival pouch for a longer period behave differently. Their position is not influenced by the eyelid movement nor by the lacrimal fluid. The release of the active ingredients can be influenced by the selection of the structural material for the embedding and can be kept constant for long periods of time. Physiologically inert polymers, for example gelatine, gelatine hardened formaldehyde, polyphenyl alcohol, polyphenyl pyrrolidon and also hydroxypropyl methyl cellulose are suitable as the structural material. To these polymers softeners can be added in order to influence the permeability and elasticity of the ocular inserts and to adapt them to the requirements. Softeners are, for example propylene glycols, glycerine, polyethylene glycol or triacetin.

The wetability and adhesive capacity of the structural substances of the ocular inserts can be optimized by the addition of amphiphile substances, for example, cholesterine or other physiologically inert surfactive substances. Examples of the applied dosage forms, include the conventional forms such as capsules, tablets, pills, multi-layered tablets and dragees. For the formulation of these oral application forms, the conventional ancillary substances are used, such as carrier and filling substances, e.g. alpha-lactose, disintegration agents such as cellulose, bonding agents such as pectin and demineralized water. The capsules are also taken into consideration with a jacket of starch or gelatine as well as with possible taste improvers.

For parenteral administration, prepared solutions for i.v. or i. m. administration can be considered, wherein in the usual manner liquid carrier substances such as water, physiological common salt solutions, glucose solutions etc. can be used. The parenteral preparations may also be prepared as emulsions or suspensions.

PHARMACOLOGICAL INVESTIGATIONS

Blood cells were extracted from 25 RP patients; 22 healthy normal persons and 26 patients with retina detachments were used as the control group. The investigation showed a significant reduction of the monapterine in lymphocytes and erythrocytes.

In FIG. 1 the content of monapterine in erythrocytes and lymphocytes of RP patients, normal healthy persons and patients with retina detachments (RD) is shown. Monapterine decreased significantly ($p<0.001$) in the lymphocytes and erythrocytes of RP patients in comparison with the other control groups.

ELECTRORETINOGRAPHY IN RATS

Respectively 8 rats (longeveans) of the male and female sex (16 rats in each group) received monapterine, dissolved to saturation in water, ad libidum for three weeks. The other groups of rats (16 rats) were given normal tap water.

The electroretinogram showed, in the case of rats who had received the monapterine in drinking water, a perceptible change.

EXAMPLES

Example 1

Ocular inserts were prepared in the following way (quantity indications in g):
polyvinyl alcohol: 0.6
polyvinyl pyrrolidone: 0.2
cholesterine: 0.05
propylene glycol: 0.2
L-monapterine: 0.1
ethyl alcohol (96 %): 2.0
water for injection purposes: 10.0

Polyvinyl alcohol was dissolved under sterile conditions in the water heated to 70° C. Cholesterine, polyvinyl pyrrolidone, the active ingredient and propylene glycol were dissolved in ethyl alcohol and the alcoholic solution was added to the aqueous solution. The batch was then poured onto a PTFE coated plate and the solvent was vapourized off. From the film thus formed, ellipsoid ocular inserts of approximately 0.8 $cm^2$ were stamped.

Example 2

For an approximately 10 ml suspension, the following were used respectively in g:
methylcellulose: 0.05
L-monapterin: 0.1
chloramphenicol: 0.05
water for injection purposes: 10.0

I claim:

1. A method for treatment of retinopathia pigmentosa comprising administering a therapeutically effective amount of a pteridine to a subject afflicted with retinopathia pigmentosa.

2. The method as claimed in claim 1, wherein said pteridine is selected from the group consisting of monapterine, sepiapterine, xanthopterine and triampterene.

3. The method as claimed in claim 1, wherein said administering is by way of oral administration.

4. The method as claimed in claim 1, wherein said administering is by way of topical administration in the eyes.

5. The method as claimed in claim 1, wherein said administering is carried out using an ocular insert.

6. The method as claimed in claim 5, wherein said pteridine is present in a slow release form in said ocular insert.

7. The method as claimed in claim 6, wherein said slow release form is a salt of said pteridine, having low solubility in water.

* * * * *